(12) United States Patent
Nishino

(10) Patent No.: US 10,307,128 B2
(45) Date of Patent: Jun. 4, 2019

(54) X-RAY IMAGING DEVICE

(71) Applicant: SHIMADZU CORPORATION, Nakagyo-ku, Kyoto-shi (JP)

(72) Inventor: Kazuyoshi Nishino, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 196 days.

(21) Appl. No.: 15/152,829

(22) Filed: May 12, 2016

(65) Prior Publication Data

US 2017/0325773 A1 Nov. 16, 2017

(51) Int. Cl.
*A61B 6/00* (2006.01)
*A61B 6/04* (2006.01)

(52) U.S. Cl.
CPC .......... *A61B 6/5241* (2013.01); *A61B 6/0457* (2013.01); *A61B 6/4452* (2013.01); *A61B 6/5258* (2013.01); *A61B 6/542* (2013.01); *A61B 6/582* (2013.01)

(58) Field of Classification Search
CPC ..... A61B 6/5241; A61B 6/5258; A61B 6/542; G06T 2207/20221
See application file for complete search history.

(56) References Cited

U.S. PATENT DOCUMENTS

| 6,097,833 | A  | * | 8/2000  | Lobregt   | A61B 6/481 |
|-----------|----|---|---------|-----------|------------|
|           |    |   |         |           | 348/E5.089 |
| 6,587,598 | B1 | * | 7/2003  | Devillers | A61B 6/5241|
|           |    |   |         |           | 382/130    |
| 6,895,106 | B2 | * | 5/2005  | Wang      | A61B 6/5241|
|           |    |   |         |           | 382/132    |
| 7,555,100 | B2 | * | 6/2009  | Wang      | A61B 6/02  |
|           |    |   |         |           | 378/98.12  |
| 7,881,434 | B2 | * | 2/2011  | Akahori   | A61B 6/4233|
|           |    |   |         |           | 378/116    |
| 8,084,744 | B2 | * | 12/2011 | Enomoto   | A61B 6/4441|
|           |    |   |         |           | 250/370.09 |
| 8,213,567 | B2 | * | 7/2012  | Sakai     | A61B 6/02  |
|           |    |   |         |           | 378/10     |

(Continued)

FOREIGN PATENT DOCUMENTS

JP 2004-236929 8/2004

*Primary Examiner* — David J Makiya
*Assistant Examiner* — Soorena Kefayati
(74) *Attorney, Agent, or Firm* — Andrew F. Young, Esq.; Lackenbach Siegel, LLP

(57) ABSTRACT

An X-ray imaging device and method acquiring a long-length image that is connected. A configuration data of the signal intensity depending on the position along a moving direction of the long-length imaging is acquired by acquiring a model data prior to the long-length imaging, to obtain an approximate configuration A long-length imaging is conducted and a brightness difference takes place along the data line in overlapping pixel regions relative to two X-ray images adjacent each other. An offset correction value C in pixels in the region other than the pixel regions from the difference Δ of pixel values in such overlapping pixel regions, the slot width D and the overlapping width d. An offset correction is conducted based on such offset correction value, C and the X-ray images following the offset correction are connected to generate the long-length imaging to obtain a long-length image that is naturally connected.

2 Claims, 12 Drawing Sheets

(56) References Cited

U.S. PATENT DOCUMENTS

| | | | | |
|---|---|---|---|---|
| 8,748,834 B2* | 6/2014 | Enomoto | ............. | A61B 6/4233 |
| | | | | 250/370.08 |
| 9,078,625 B2* | 7/2015 | Kappler | ................ | A61B 6/563 |
| 9,541,509 B2* | 1/2017 | Akahori | ................ | A61B 6/486 |
| 9,582,940 B2* | 2/2017 | Yu | ........................ | A61B 8/5238 |
| 9,697,923 B2* | 7/2017 | Tsuji | .................... | A61B 6/4266 |
| 2005/0129299 A1* | 6/2005 | Kreang-Arekul | ........ | G06K 9/32 |
| | | | | 382/132 |
| 2006/0018527 A1* | 1/2006 | Bojer | .................... | G06T 3/4038 |
| | | | | 382/132 |
| 2011/0228900 A1* | 9/2011 | Sakai | ...................... | A61B 6/02 |
| | | | | 378/10 |
| 2013/0315372 A1* | 11/2013 | Behiels | .................... | A61B 6/06 |
| | | | | 378/62 |
| 2013/0331725 A1* | 12/2013 | Noji | ..................... | A61B 6/5217 |
| | | | | 600/534 |
| 2014/0003578 A1* | 1/2014 | Omote | ................... | G01N 23/04 |
| | | | | 378/63 |
| 2016/0134818 A1* | 5/2016 | Iwashita | ............. | A61B 6/4233 |
| | | | | 348/162 |
| 2016/0247325 A1* | 8/2016 | Yu | ........................ | A61B 8/5238 |
| 2016/0278729 A1* | 9/2016 | Iijima | ................. | A61B 6/4208 |
| 2016/0350925 A1* | 12/2016 | Moon | ....................... | G06T 3/20 |

* cited by examiner

X-RAY IMAGING DEVICE

BACKGROUND OF THE INVENTION

Field of the Invention

The present invention relates to, but does not claim priority from, JP Ser. No. 2013-245379 filed Nov. 27, 2013 and published as JP Ser. No. 2015-100642 on Jun. 4, 2016, the entire contents of which are incorporated by reference.

FIGURE SELECTED FOR PUBLICATION

FIG. 6

Description of the Related Art

The present invention relates to an X-ray imaging device for X-ray imaging and particularly relates to the technology that generates a long-length image by a method of connecting a plurality of X-ray images.

Conventionally, relative to such device, a X-ray tube (X-ray radiation means) and a X-ray detector (X-ray detection means) moving along the direction of body axis of the subject are synchronously-operated so as to acquire X-ray images respectively and the acquired X-ray images are connected in the body axis direction to generate the long-length image. Particularly, the method for conducting long-length imaging to generate a long-length image by connecting X-ray images, which are acquired by squeezing the radiated visual field like a slit while adjusting the open-degree of the X-ray by a collimater, in the body axis direction (hereafter, "slot imaging") is disclosed (e.g., in Patent Document 1, noted below.)

The image synthesis method (image connection method) according to the conventional slot imaging connects, when the imaging condition is constant, the overlapping pixel regions (superimposing portion) between two X-ray images adjacent each other (front-and-back) so as to make pixel values smooth by e.g., interpolation calculation and so forth. When the imaging condition varies every imaging, the method, which is executed to connect after each X-ray brightness is uniformly-converted every objective X-ray image based on each imaging condition or signal intensity profile of overlapping region, is known.

PATENT DOCUMENT

Patent Document: Laid Open JP 2004-236929, the entire contents of which are incorporated herein by reference.

Aspects and Summary of the Invention

However, even when the imaging condition is constant, the stripped pattern, referring to FIG. 9, may appear in the (synthesized) long-length image based on the conventional connection method.

In addition, FIG. 9 is illustrating the long-length image of uniform material like an acrylic board and it is confirmed that an imaging even such uniform material like an acrylic board may provide a stripped pattern.

Considering such circumstances, the object of the present invention is to provide an X-ray imaging device capable of acquiring a long-length image naturally connected.

Means for Solving the Problem

The inventor of the present invention studied extensively to solve the above problem and found the following solutions.

Specifically, according to the result shown in FIG. 9, it is found that a surprising phenomenon, in which the brightness variation (pixel value variation) due to the change of the offset value relative to the region where is under the strong direct-ray, takes place. During a slot imaging, the X-ray detector is set as the data line of the X-ray detector is parallel to the direction of body axis (connection direction), the X-ray detector and the X-ray tube are moved as parallel to the data line and then a plurality of X-ray images acquired by the X-ray detector is connected. Accordingly, it can be confirmed that the phenomenon, in which the brightness varies (pixel value variation) along the data lines, takes place from the result shown in FIG. 9. Particularly, when the region under almost no X-ray and the region under storing X-ray (under the direct ray) exist in the one plan of the X-ray detector as the slot imaging is conducted, such phenomenon is obvious.

FIG. 10 is illustrating the profile of signal intensity relative to the long-length image and the upper graph is illustrating the case of broad slot width, the middle graph is illustrating the case of slightly narrow slot width and the lower graph is illustrating the case of narrow slot width used when the actual slot imaging is conducted. The upper graph in the case of the broad slot width provides the even profile but the lower graph in the case of the narrow slot width, which is used when the actual slot imaging is conducted, provides a complex pattern relative to the brightness variation (pixel value variation) at the central region.

However, even when the imaging condition is constant, the stripped pattern, as set forth referring to FIG. 9, may appear in the long-length image based on the conventional connection method without correction of brightness variation due to the incident direct ray. On the other hand, referring to FIG. 11, it is confirmed that such phenomenon depends on the amount of the incident direct ray because no stripped pattern takes place when narrowed thereof in the direction perpendicular to the body axis so as to restrict the incident direct ray. Then, referring to FIG. 11, the slot imaging narrowed in the direction perpendicular to the body axis can be optional so as to restrict the incident direct ray. However, such slot imaging, on which narrowed in the direction perpendicular to the body axis, it is not desirable because the information as to the edge region is not reflected when the X-ray imaging is conducted on the subject having bend back bone.

Meantime, such phenomenon other than the incident direct ray may take place when the time needed to read out pixel values from the sensor of X-ray detector takes place as a time lag between the read-out at the first gate line and the read-out at the last gate line relative to the slit-like image and it is considered, as the cause, that the offset value caused due to the time lag thereof varies depending on the move direction (i.e., the direction along the data line) of the long-length imaging. Specifically, referring to FIG. 12, the time lag takes place between the time tSTART at which when the pixel value at the first gate line GSTART is read out along the data line D and the time tEND at which the pixel value at the last gate line GEND is read out along the data line D and as results, the offset value varies along the data line D. In addition, the sign MUX in FIG. 12 stands for multiplexer.

Then, the inventor additionally discovered that an offset correction based on the profile of pixel values instead of the method to restrict the incident direct ray can restrict the brightness variation (pixel value variation) depending on the position of the gate line and the image naturally connected can be obtained, accordingly with an improved benefit.

The present invention based on such finding constitutes the following structure. Specifically, an X-ray imaging device of the present invention is an X-ray imaging device that conducts an X-ray imaging comprises; an X-ray irradiation means that irradiates X-ray to a subject; a detection means that detects the X-ray transmitted through the subject; when a plurality of X-ray images acquired by the X-ray detection means is connected to generate a long-length image, an image connection means that acquires and connects the plurality of X-ray images by the X-ray detection means while moving parallel to the data line of the X-ray detection means; a configuration data storage means that stores the configuration data of the signal intensity, which is the model data predetermined prior to the long-length imaging, depending on the position along the moving direction of the long-length imaging; an offset correction value calculation means that calculates the offset correction value depending on the position along the move direction of the long-length imaging based on the configuration data of the signal intensity stored by the configuration data storage means and the difference of pixel values in the overlapping pixel region relative to two X-ray images adjacent each other as to the subject; and an offset correction means that generates an X-ray image following each offset correction, which executes respectively the processing to subtract the offset value, every data line, depending on the position corresponding to the pixel of such pixel values from the objective pixel values relative to the X-ray image, in place in the upper side of the move direction, of two adjacent X-ray images each other relative to the subject; wherein the image connection means conducts the long-length imaging by connecting the X-ray images following the offset correction was provided by the offset correction means.

Effect of Invention

According to the X-ray imaging device of the present invention, an X-ray detection means that acquires and connects a plurality of X-ray images by the X-ray detection means while moving parallel to the data line of the X-ray detection means when a plurality of X-ray images acquired by the X-ray detection means is connected to generate a long-length image. As results, the brightness variation (pixel value variation) along the data line takes place and the stripped pattern takes place in the long-length image under the strong direct ray when no correction is executed. Such brightness variation (pixel value variation) does not change much the characteristics corresponding to the data-line or the connection position and the configuration of the signal intensity depending on the position along the move direction of the long-length imaging is deemed constant except a gradient and so on. For example, when the signal intensity varies with a linear configuration relative to the position thereof, it is considered that the signal intensity may vary also with a linear configuration relative to the other position (data line or connection position.) In contrast, for example, when the signal intensity varies with quadratic curve relative to the position thereof, the signal intensity may vary also with quadratic curve relative to the other position.

Accordingly, a phantom (e.g., acrylic board) and so forth is applied to acquire the model data prior to the long-length imaging in order to obtain the approximate configuration. A configuration data storage device stores the configuration data of the signal intensity depending on the position along the moving direction of the long-length imaging. Next, the long-length imaging is conducted by that the X-ray irradiation means irradiates an X-ray to the subject, the X-ray detection means detects the X-ray transmitted through the subject, the X-ray detection means respectively acquires and connects a plurality of X-ray images relative to the subject while moving parallel to the data line of the X-ray detection means in order to generate the long-length image relative to the subject. Relative to the X-ray image obtained by the long-length imaging as to the subject, the overlapping pixel regions relative to two X-ray images adjacent each other should naturally have the same brightness (pixel values) because the region thereof are adjacent images but the brightness difference (difference of pixel values) takes place due to the brightness variation (variation of pixel values) along the data line. Such difference is the variation of the offset value (offset correction value.) In this way, the difference is acquired so that the variation depending on the position at the objective data line can be acquired. In addition, the difference is acquired and the information relative to the subject is canceled so that the brightness variation pixel value variation) along the data line can be purely acquired.

In addition, according to the configuration data of the signal intensity stored in the configuration data storage means, the offset correction value calculation means can calculate the offset correction value relative to the pixels in the region other than the overlapping pixel regions from the difference of pixel values in such overlapping pixel regions described above. Further, the offset correction means; which executes respectively the processing to subtract the offset value, every data line, depending on the position corresponding to the pixel of such pixel values from the objective pixel values relative to the X-ray image, in place in the upper side of the move direction, of two adjacent X-ray images each other relative to the subject; generates an X-ray image following each offset correction. The image connection means connects the X-ray images, following the offset correction, acquired by such offset correction means and generates the long-length imaging so that the long-length image, for which the X-ray images restricting the variation of brightness (pixel value variation) depending on the position of the gate line are connected, can be obtained. As results, the long-length image naturally connected can be obtained.

Effect of the Invention

According to the X-ray imaging device of the present invention, the model data is acquired prior to the long-length imaging in order to obtain the approximate configuration and the configuration data of the signal intensity depending on the position along the move direction of the long-length imaging is stored in the configuration data storage means. Next, the long-length imaging as to the subject is conducted and a brightness difference (difference of pixel values) takes place due to the brightness variation (variation of pixel values) along the data line in the overlapping pixel regions relative to two X-ray images adjacent each other. In addition, according to the configuration data of the signal intensity stored in the configuration data storage means, the offset correction value calculation means can calculate the offset correction value relative to the pixels in the region other than the overlapping pixel regions from the difference of pixel values in such overlapping pixel regions described above. Further, the offset correction means; which executes respectively the processing to subtract the offset value, every data line, depending on the position corresponding to the pixel of such pixel values from the objective pixel values relative to the X-ray image, in place in the upper side of the move direction, of two adjacent X-ray images each other relative to the subject; generates an X-ray image following each offset correction; The image connection means connects the X-ray images obtained by such offset correction means, following the offset correction and generates the long-length imaging so that the long-length image naturally connected can be obtained.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
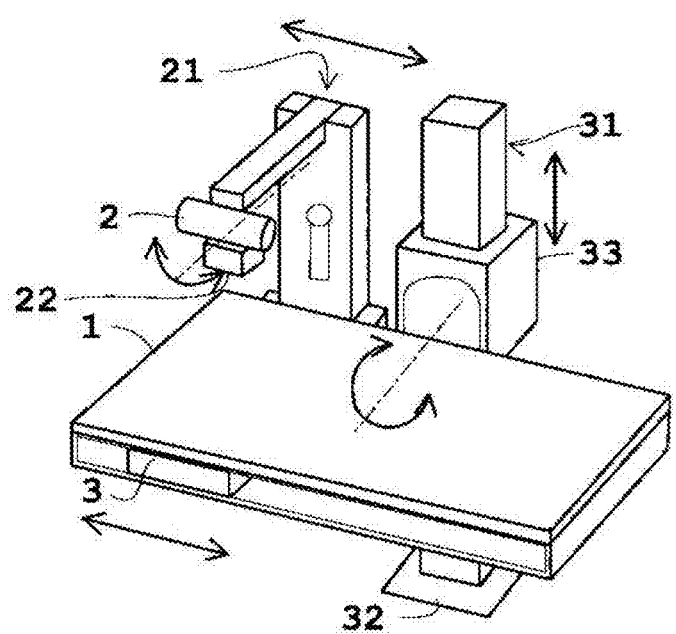
FIG. 1 is a schematic perspective view illustrating an X-ray imaging device of the Embodiment.

Reference will now be made in detail to embodiments of the invention. Wherever possible, same or similar reference numerals are used in the drawings and the description to refer to the same or like parts or steps. The drawings are in simplified form and are not to precise scale. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

Embodiment

Referring to Figures, the inventors illustrate Embodiment of the present invention.

Figure 2:
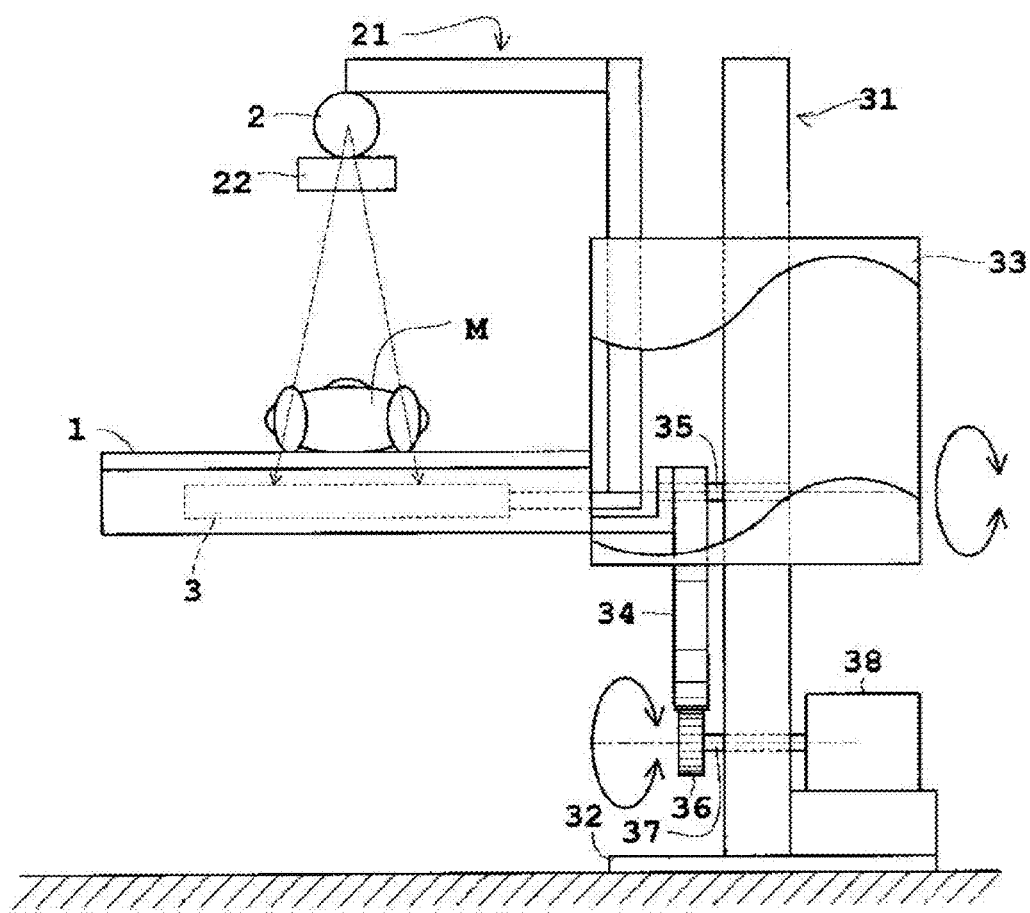
FIG. 2 is a schematic front view illustrating an X-ray imaging device of the Embodiment.
Figure 3:
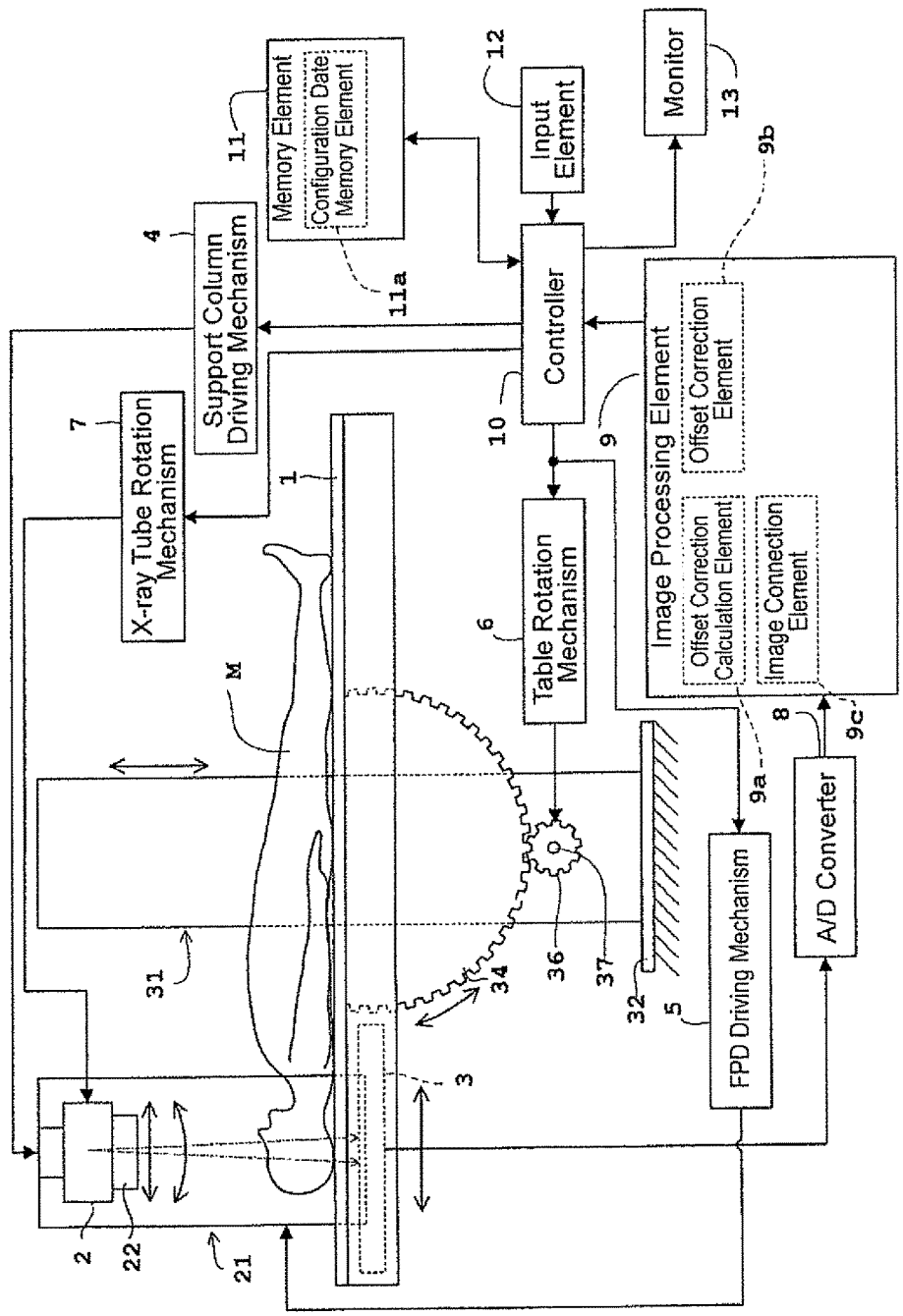
FIG. 3 is a schematic side view and a block diagram illustrating an X-ray imaging device of the Embodiment.

FIG. 1 is a schematic perspective view illustrating an X-ray imaging device of the Embodiment, FIG. 2 is a schematic front view illustrating an X-ray imaging device of the Embodiment and FIG. 3 is a schematic side view and a block diagram illustrating an X-ray imaging device of the Embodiment. A table supporting element and so forth are not shown in FIG. 3.

Referring to FIG. 1-FIG. 3, an X-ray imaging device comprises a table 1 on which a subject M is laid, an X-ray tube 2 to irradiate X-ray to the subject M and the flat panel type X-ray detector (FPD) 3 to detect the X-ray transmitted through the subject M. FPD 3 is installed inside the table 1. The X-ray tube 2 corresponds to the X-ray irradiation means of the present invention and the flat panel type X-ray detector (FPD) corresponds to the detection means of the present invention.

The X-ray imaging device comprises a support column 21 to support the X-ray tube 2 and a main support column 31 to support the table 1. A collimater 22 that controls the bright visual field by adjusting the open-degree of the X-ray irradiated from the X-ray tube 2 is installed in the irradiation side of the X-ray tube 2. According to the present Embodiment, one end of the main support column 31 supports the X-ray tube 2 as described above and the other end supports the FPD 3 installed inside the table 1 so that the X-ray tube 2 and the FPD 3 move in the same direction and parallel to the table 1 along the longitudinal direction of the subject M (refer to FIG. 3.) In addition, while the X-ray tube 2 and the FPD 3 are moving in the same direction and parallel to the table 1 along the longitudinal direction of the subject M, the slit-like X-ray is irradiated from the X-ray tube 2 and the FPD 3 detects the X-ray to conduct X-ray imaging under the squeezed narrower condition (refer to FIG. 3) than the bright visual field projected on the FPD 3 by the collimator 22.

The main support column 31 is installed vertically on the base 32 installed on the floor surface, to which the table holding element 33 is mounted so as to be capable of up-and-down (tilting) the table 1. The main support column 31 is installed vertically on the base 32 installed on the floor surface and the table holding element 33 is installed to hold the table 1 so that the FPD 3 installed inside the table 1, the support column 21 holding the FPD 3 at the other end, the X-ray tube 2 supported at the one end of the support column 21 and the collimater installed in the irradiation side of the X-ray tube 2 can be supported.

The table holding element 33 comprises a fan-shaped rack 34 that rotates and tilts the table 1 around the center of axis of the horizontal axis, a spindle 35 inserted into the fan-shaped rack 34 and the main support column 31, a pinion 36 fit into the fan-shaped rack 34, a rotation shaft 37 having the pinion 36 at the one end thereof and a motor 38 that rotates the rotation shaft 37 therein. The motor 38 rotates the rotation shaft 37 so that the pinion 36, mounted to the one end of the rotation shaft 37, can rotate and then the fan-shaped rack 34 fit therein rotates, in interlock with the rotation of the pinion 36, around the spindle 35 as the spindle 35 is the fulcrum therefore. The fan-shaped rack 34 rotates around the spindle 35 so that the table 1 can be rotated and tilted around the center of axis of the horizontal axis.

In this way, when the table 1 rotates and tilts around the center of axis of the horizontal axis, the table 1 can take an upright posture, a tilted posture and a horizontal posture (recumbent posture) by up-and-down operation. In addition, the supporting column 21 tilts along with that the x-ray tube 2 the X-ray tube 2 and the FPD 3 tilts, in interlock with the tilt of the table 1. Further, when the table 1 is tilted into the upright posture and the distance from the rotation position around the center of axis of the horizontal axis of the table 1 to the lower region of the table 1 is longer than the height from the spindle 35 of the support column 31 to the lower region of the support column 31, the upright posture cannot be brought in reality but in this case, if the table 1 is moved to the upper region, the upright posture can be brought in reality.

The X-ray imaging device, referring to FIG. 3, comprises; others including a support column driving mechanism 4 that drives a motor (not shown in FIG.) in order to move the support column 21 along with the X-ray tube 2 and the collimater 22 supported thereby parallel to the table 1 along the longitudinal direction, which is the body axis of the subject M; a FPD driving mechanism 5 that drives the motor (not shown in FIG.) in order to move the FPD 3 parallel to the table 1 along the longitudinal direction; a table rotation mechanism 6 that drives the motor 38 (refer to FIG. 2) in order to operate the table 1 described above up-and-down (tilting); an X-ray tube rotation mechanism 7 that drives the motor (not shown in FIG.) in order to rotationally move the X-ray tube 2 around the center of axis of the connected axis (i.e., axis perpendicular to the body axis); an A/D converter 8 in order to digitize the X-ray detection signal, a charge signal, and take out from the FPD 3; an image processing element 9 that executes a variety of processings based on the X-ray detection signal output from the A/D/converter 8; a controller 10 that controls each element overall; a memory element 11 that stores the processed X-ray image and so forth; an input element 12, to which the operator sets the input; a monitor 13 that displays the processed X-ray image and so forth; and so forth. Meantime, a high voltage generator that generates the tube voltage of the X-ray tube 2 and the tube current and so forth are not illustrated because of not related characteristic property per se.

The image processing element 9 comprises; an offset correction value calculation element 9a that calculates the offset correction value depending on the position along the move direction of long-length imaging based on the difference of pixel values in the overlapping pixel region in the two adjacent X-ray images each other relative to the configuration data of the signal intensity stored in the configuration data memory element 11a, described later, and the subject M; an offset correction element 9b that generates an X-ray image following each offset correction, which executes respectively the processing to subtract the offset value, every data line 49 (refer to FIG. 4. FIG. 5), described later, depending on the position corresponding to the pixel of such pixel values from the objective pixel values relative to the X-ray image, which is in place in the upper side of the move direction, of two adjacent X-ray images each other relative to the subject M; and an image connection element 9c that connects the plurality of X-ray images obtained by the FPD 3 to generate the long-length image. Meantime, the FPD 3 acquires and connects a plurality of X-ray images while the FPD 3 is moving parallel to the data line 49 when the image connection element 9c connects the plurality of X-ray images to generate the long-length image. The offset correction value calculation element 9a corresponds to the offset correction calculation means of the present invention and the offset correction element 9b corresponds to the offset correction means of the present invention and the image connection element 9c corresponds to the image connection means of the present invention. The specific function of the offset correction calculation element 9a, the offset correction element 9b and the image connection element 9c will be set forth later referring to FIG. 6, FIG. 7.

The controller 10 comprises a central processing unit (CPU) and so forth and the memory element 11 comprises memory media typically including a ROM (read-only memory), a RAM (random-access memory) and so forth. In addition, the input element 12 comprises a pointing device represented by a mouse, a keyboard, a joy stick, a trackball and a touch panel and so forth. The X-ray imaging device is operable to conduct an X-ray imaging of the subject M by that the FPD 3 detects X-rays transmitted through the subject M and then the image processing element 9 executes the image processing based on the detected X-rays to generate the X-ray image.

According to the present Embodiment, the memory element 11 comprises a configuration data storage element 11a that stores the configuration data of the signal intensity, which is the model data predetermined prior to the long-length imaging, depending on the position along the moving direction of the long-length imaging. The configuration data storage element 11a corresponds to the configuration data storage means of the present invention. The specific function of the configuration data storage element 11a is also set forth later referring to FIG. 6, FIG. 7.

Figure 4:
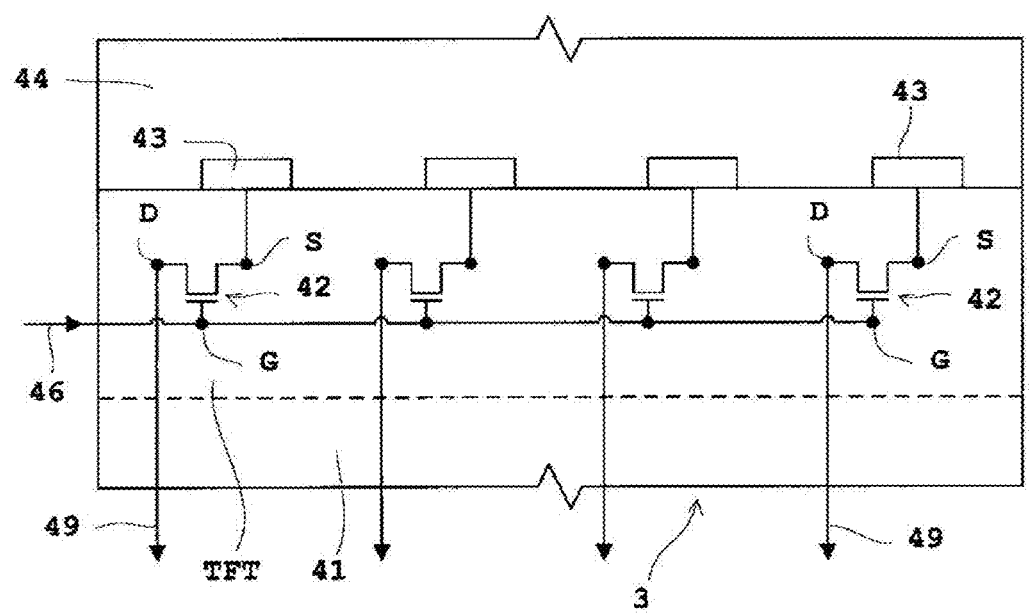
FIG. 4 is a side view illustrating an equivalent circuit of the flat panel type X-ray detector (FPD.)
Figure 5:
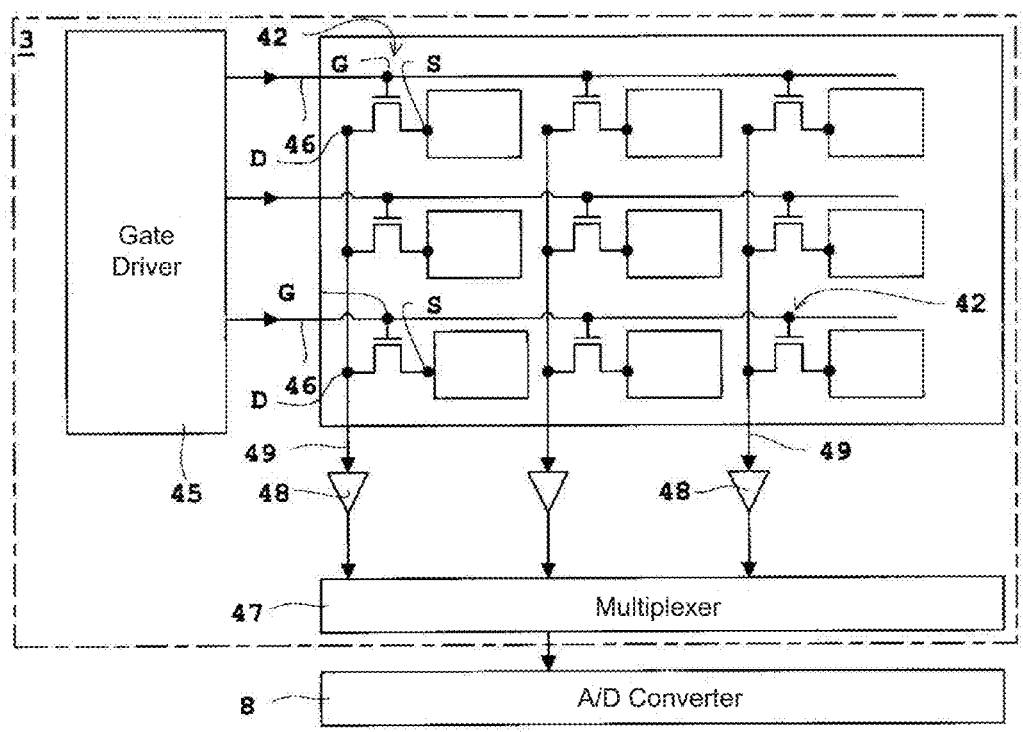
FIG. 5 is a plan view illustrating an equivalent circuit of the flat panel type X-ray detector (FPD.)

Next, the inventor sets forth the structure of the flat panel type X-ray detector (FPD 3) referring to FIG. 4, FIG. 5. FIG. 4 is a side view illustrating an equivalent circuit of the flat panel type X-ray detector (FPD) and FIG. 5 is a plan view illustrating an equivalent circuit of the flat panel type X-ray detector (FPD.)

Referring to FIG. 4, the FPD 3 comprises a glass base board 41 and a thin film transistor TFT formed on the glass board 41. Referring to FIG. 4, FIG. 5, with regard to the thin film transistor TFT, a number of switching elements 42 (e.g., 1024×1024) is arranged in a two-dimensional matrix in a plane and the switching elements 42 are separately formed every carrier collection electrode 43. Specifically, the FPD 3 is also a two-dimensional array radiation detector.

Referring to FIG. 4, an X-ray-sensitive semiconductor 44 is laminate-molded on the carrier collection electrode 43 and, referring to FIG. 4, FIG. 5, the carrier collection electrode 43 is connected to a source S of the switching element 42. A plurality of gate lines 46 is connected to the gate driver 45 each gate line 46 is also connected to the gate G of the switching element 42. On the other hand, referring to FIG. 5, a plurality of data lines 49 is connected to the multiplexer 47, which collects electric signals and outputs the single signal therefrom, through an amplifier 48 and, referring to FIG. 4, FIG. 5, each data line 49 is connected to the drain D of the switching element 42. The data line 49 corresponds to the data line of the present invention.

The voltage of the gate line 46 is applied (or done to 0V) under the state of applying the bias voltage to the common electrode, not shown in FIG., so that the gate of switching element 42 is turned on and the carrier collection electrode 43 reads out the electric charge signal (carrier) converted from the incident X-ray in the detection side via the X-ray sensitive semiconductor 44 to the data line 49 via the source S and the drain D of the switching element 42. In addition, the electric charge signal is temporarily accumulated and stored in the capacitor (not shown in FIG.) until the switching element is turned on. The electric charge signals read out to each data line 49 are amplified by the amplifier 48 and the multiplexer 47 output together as one electric charge signal. Output electric charge signals are digitized by the A/D converter 8 and output as X-ray detection signals.

Figure 6:
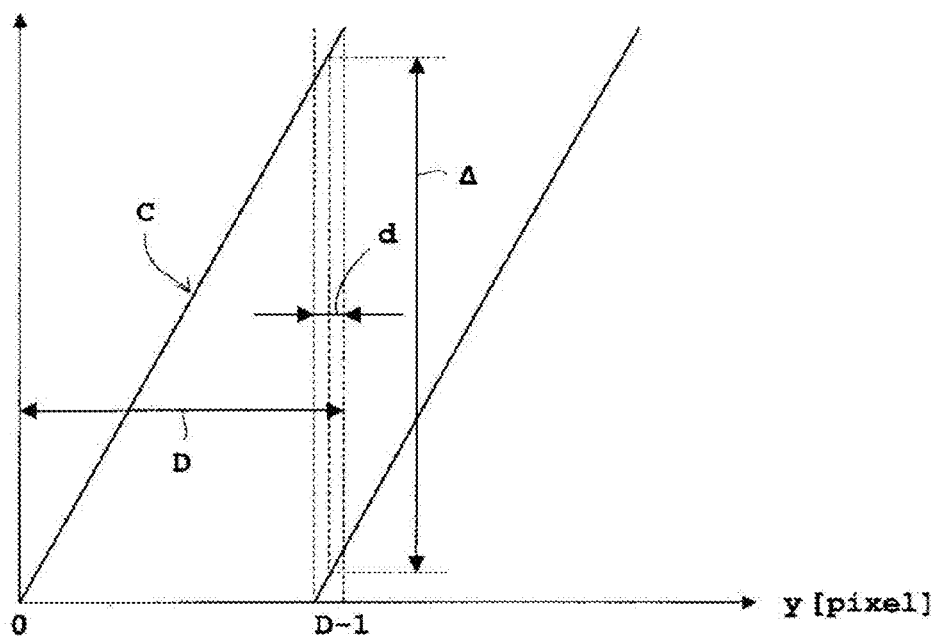
FIG. 6 is a schematic view illustrating the profile showing the relationship between the offset correction value, the difference of the pixel value in the overlapped pixel region and the slot width, which is the width of the X-ray image along the connection direction, when the signal intensity increases in a linear configuration relative to the position along the move direction of the long-length imaging.
Figure 7:
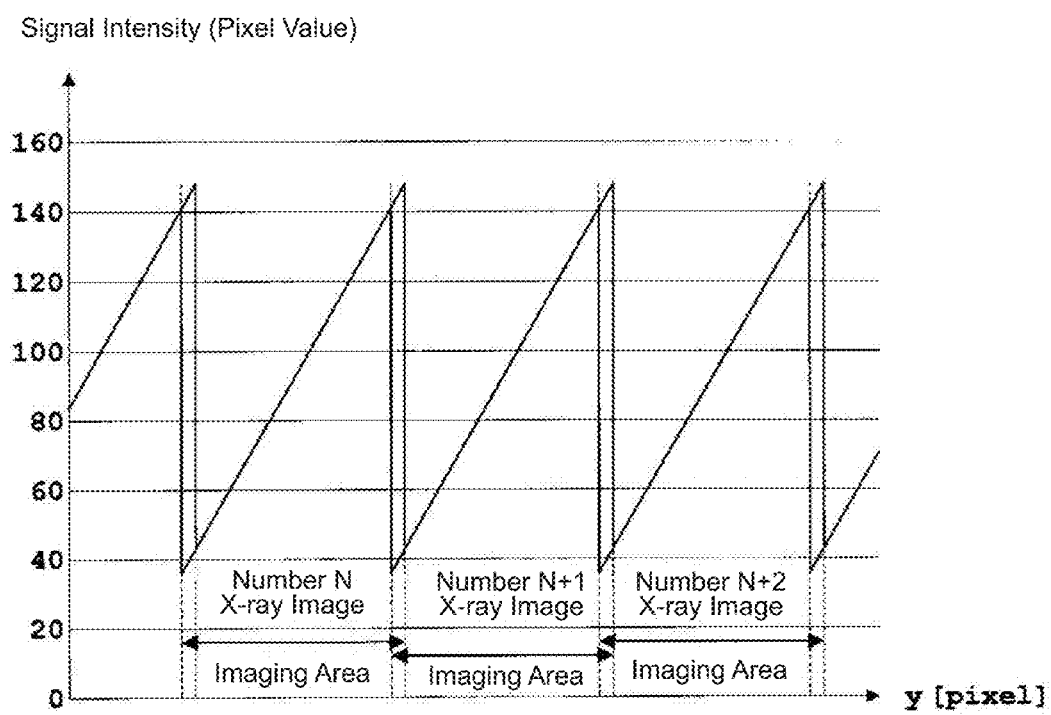
FIG. 7 is a schematic view illustrating the profile relative to an X-ray image when the signal intensity increases in a linear configuration relative to the position along the move direction of the long-length imaging.

Next, the inventor sets forth specific functions of the specific function of the offset correction calculation element 9a, the offset correction element 9b and the image connection element 9c and the configuration data storage element 11a referring to FIG. 6, FIG. 7. FIG. 6 is a schematic view illustrating the profile showing the relationship between the offset correction value, the difference of the pixel value in the overlapped pixel region and the slot width, which is the width of X-ray image along the connection direction, when the signal intensity increases in a linear configuration relative to the position along the move direction of the long-length imaging, and FIG. 7 is a schematic view illustrating the profile relative to an X-ray image when the signal intensity increases in a linear configuration relative to the position along the move direction of the long-length imaging.

First, a phantom (e.g., acrylic board) and so forth is applied to acquire the model data prior to the long-length imaging. The X-ray image relative to the phantom is acquired by imaging the phantom, which is formed from the acrylic board and so forth, using the same slot width as the long-length imaging therefor as to the slot width that is the width of the X-ray image along the connection direction (i.e., slot width in the longitudinal direction) by irradiating the same X-ray dosage as the dosage for the long-length imaging from the X-ray tube 2 (referring to FIG. 1-FIG. 3) under the same imaging condition as the condition for the long-length imaging. The purpose of acquiring the X-ray image relative to the phantom is to investigate the configuration of the signal intensity depending on the position along the move direction of the long-length imaging.

First, the broad phantom in the direction perpendicular to the body axis is prepared so that the incident direct ray to the FPD 3 (referring to FIG. 1-FIG. 3) can gradually intensify and the X-ray image is acquired using the prepared phantom and the profile of the signal intensity as the data line is the horizontal axis is generated. The offset value relative to the profile of the signal intensify obtained first does not vary independently along the data line but the offset value varies along the data line relative to somewhat narrowed phantom when the profile of each signal intensify is generated while successively preparing phantoms of which the direction perpendicular to the body axis gradually narrows. Referring to FIG. 6, FIG. 7, the configuration data of the signal intensity depending on the position along the move direction of the long-length imaging can be obtained as the profile of the signal intensity when the signal intensity increased in the linear configuration relative to the position along the move direction of the long-length imaging. The configuration data of such signal intensity is written temporarily in the configuration data storage element 11a (refer to FIG. 3.)

In addition, the inventor set forth the case, in which the profile of each signal intensify is generated while successively preparing phantoms of which the direction perpendicular to the body axis gradually narrows as the incident direct ray can gradually intensify, but the invention is not limited to such generation method. The profile of signal intensity can be generated by irradiating X-ray to the phantom under the state in which the opening width of the collimater 22 (refer to FIG. 1-FIG. 3) is narrowed in the perpendicular direction to the body axis first as the incident direct ray can gradually intensify and then each profile of signal intensity can be generated by boarding gradually the opening width of the collimator 22 as the direction perpendicular to the body axis broadens gradually.

In this way, when the approximate configuration is obtained from the profile of the signal intensity is obtained by acquiring the X-ray image relative to the phantom, the configuration of the signal intensity depending on the position along the move direction of the long-length imaging is deemed to be the constant configuration excluding the gradient. Here, the inventor sets forth the case in which the signal intensity increases in the linear configuration relative to the position along the move direction of the long-length imaging and when the X-ray image relative to the phantom is acquired, the data of the model in which the signal intensity increased relative to such position in the linear configuration can be obtained and it is deemed that other regions (data line or connection position) also vary in the linear configuration even relative to the long-length imaging.

Next, the long-length imaging of the subject M is conducted according to that; the X-ray tube irradiates X-ray to the subject M (refer to FIG. 2, FIG. 3), the FPD 3 detects the X-ray transmitted the subject M, the FPD 3 acquires and connects a plurality of X-ray images respectively relative to the subject M while moving parallel to the data line of the FPD 3; and the image connection element 9c (refer to FIG. 3) generate the long-length image relative to the subject M. In addition, in practice, after the offset correction described later, the long-length image can be generated following the connection.

Relative to the X-ray image obtained by the long-length imaging as to the subject M, referring to FIG. 6, two X-ray images adjacent each other (X-ray image number N in FIG. 7 and X-ray image number N+1 in FIG. 7) should naturally have the same brightness (same pixel values) because the region thereof are adjacent images but the brightness difference (difference of pixel values) takes place due to the brightness variation (variation of pixel values) along the data line. Referring to FIG. 7, the difference thereof is approximately 100 pixel values.

Referring to FIG. 6, the difference of the pixel values (difference at the center point of overlapping pixel regions in FIG. 6) in the overlapping pixel region, relative to two X-ray images adjacent each other (X-ray image number N and X-ray image number N+1), is $\Delta$. In addition, the slot width that is the width of X-ray image along the connection direction is a pixel D and the overlapping pixel thereof is a pixel d. Further, the pixel coordinate of the X-ray image (X-ray image number N) in the upper side of the move direction and when the pixel coordinate is moved in the range of y=0 to D−1, the offset correction value is C. If the signal intensity increases in a linear configuration relative to the position along the move direction of the long-length imaging, the offset value is represented by the following formula (1).

$$C = \Delta/(D-d) \times y \tag{1}$$

Referring to the above formula (1), it is obvious that the above formula (1) is a linear function relative to the pixel coordinate y having the gradient $\Delta/(D-d)$.

Accordingly, if the model data is acquired using a phantom and so forth prior to the long-length imaging, an approximate configuration (in this case, a configuration of linear function in which the signal intensity increases in the linear configuration relative to the position along the move direction of the long-length imaging) and if an actual gradient Δ/(D−d) is obtained every data line or connection position relative to the long-length imaging, the offset correction value C depending on the position along the move direction of the long-length imaging. In this way, an offset correction value calculation element 9a (refer to FIG. 3) can calculate the offset correction value C depending on the position along the move direction of the long-length imaging from the above formula (1) based on the configuration data of the signal intensity stored by the configuration data storage element 11a and the difference Δ of pixel values in the overlapping pixel region relative to two X-ray images (X-ray image number N, X-ray image number N+1) adjacent each other as to the subject M.

Further, the offset correction element 9b (refer to FIG. 1) generates an X-ray image following offset correction, which executes respectively the processing, relative to every data line, to subtract the offset value C, depending on the position corresponding to the pixel of such pixel values (pixel coordinate y), from the objective pixel values relative to the X-ray image (X-ray image number N), in place in the upper side of the move direction, of two adjacent X-ray images (X-ray image number N, X-ray image number N+1) each other relative to the subject M. The image connection element 9e connects the X-ray images, following the offset correction, obtained by such offset correction element 9b to generate the long-length image, finally.

Figure 8:
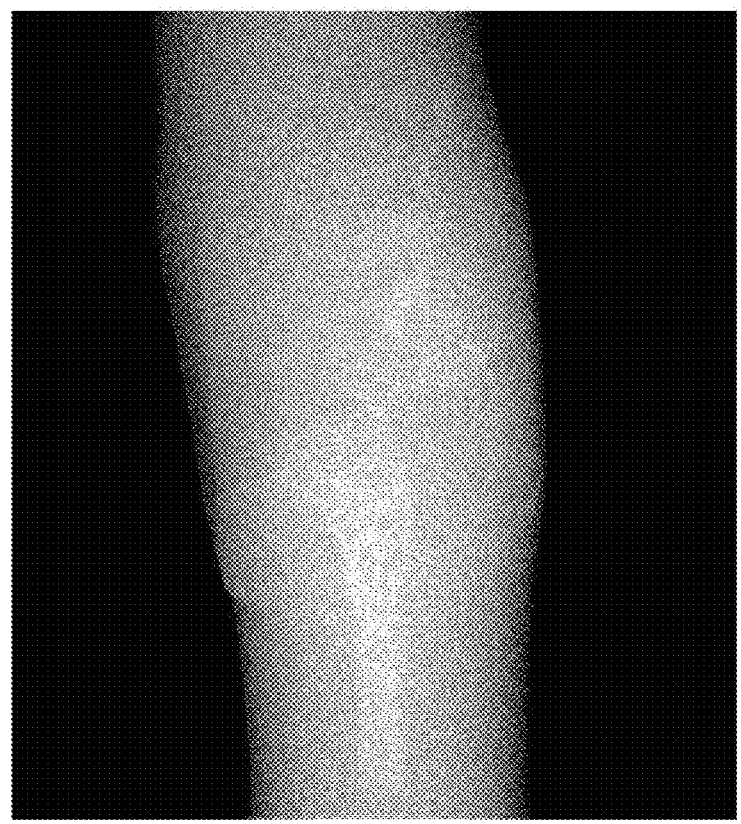
FIG. 8 is an image after the offset correction.
Figure 9:
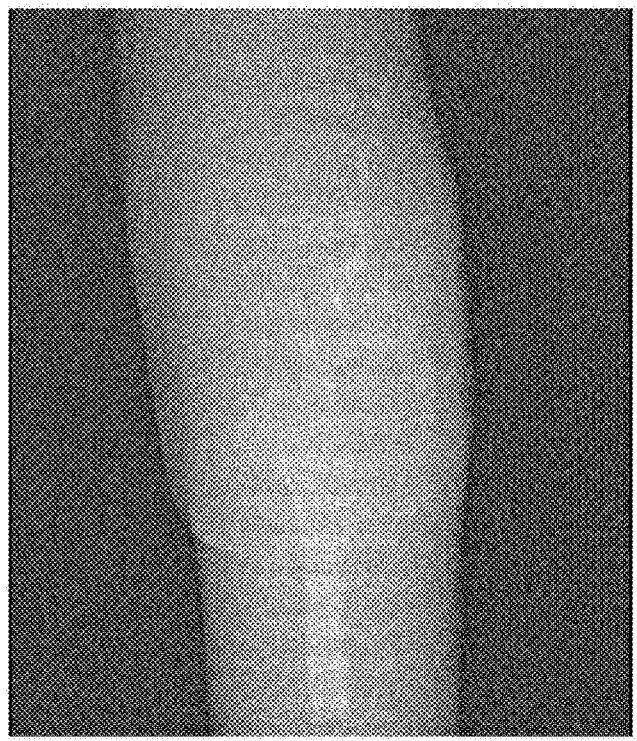
FIG. 9 is an image obtained with the incident direct ray (direct ray incident image.)
Figure 10:
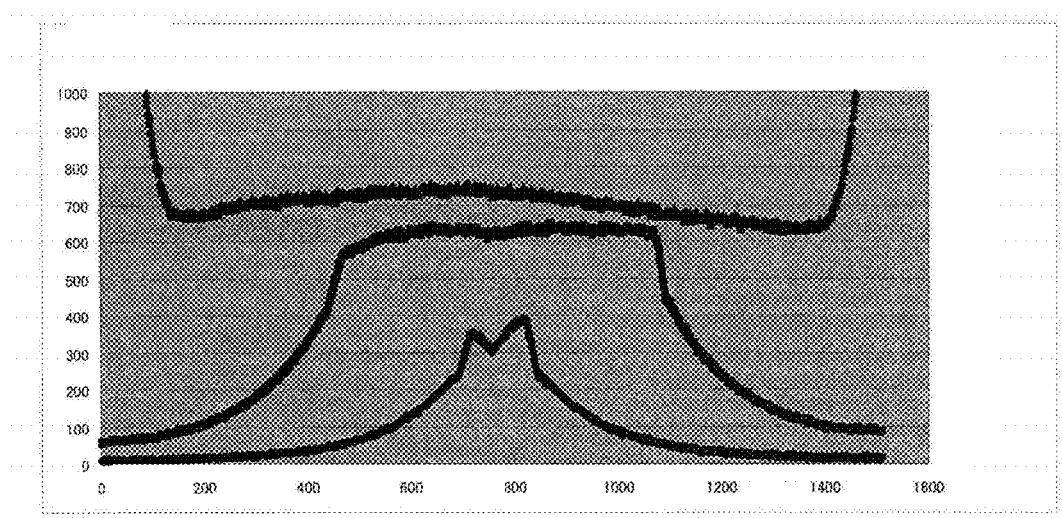
FIG. 10 is a profile of the signal intensity relative to the long-length image.
Figure 11:
FIG. 11 is an image obtained by restricting the incident direct ray (direct ray restriction image.)
Figure 12:
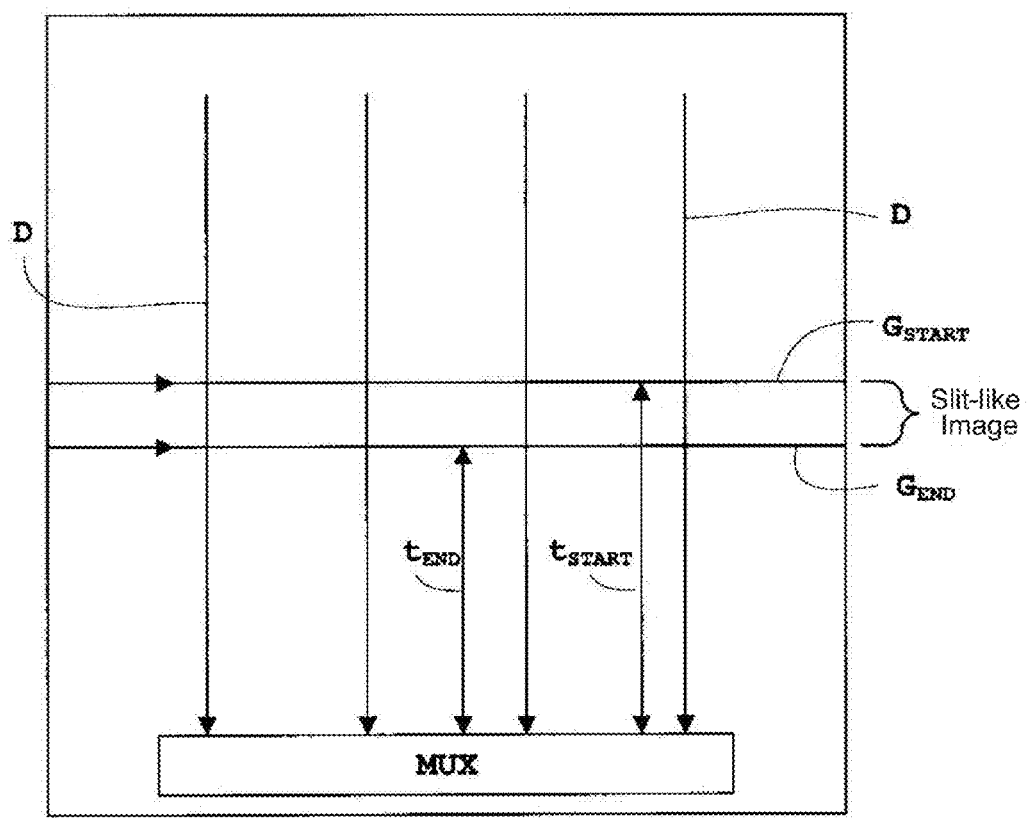
FIG. 12 is a schematic view illustrating the gate line and the data line being provided with setting forth variation of the offset value.

FIG. 8 is an example image after the offset correction, wherein the long-length synthesis (image connection) was conducted following the offset correction. According to the result in FIG. 8, it is confirmed that a naturally connected long-length image, referring FIG. 9, with no stripped pattern is acquired without restricting the incident direct ray.

According to the X-ray imaging device of the present invention, a plurality of X-ray images is acquired by the FPD 3 and connected respectively while moving parallel to the data line 49 of the FPD 3 (referring to FIG. 4, FIG. 5) when a plurality of X-ray images acquired by the flat panel type X-ray detector (FPD 3) is connected to generate a long-length image. As results, the brightness variation (pixel value variation) along the data line 49 takes place and the stripped pattern takes place in the long-length image under the strong direct ray when no correction is executed. Such brightness variation (pixel value variation) does not change much the characteristics corresponding to the data-line 49 or the connection position and the configuration of the signal intensity depending on the position along the move direction of the long-length imaging is deemed constant except gradient (Δ/(D−d) in the above formula (1)) and so on. For example, when the signal intensity varies with a linear configuration relative to the position thereof, the signal intensity may vary also with a linear configuration relative to the other position (data line or connection position.) In contrast, for example, when the signal intensity varies with quadratic curve relative to the position thereof, the signal intensity may vary also with quadratic curve relative to the other position.

Accordingly, a phantom (e.g., acrylic board) and so forth is applied to acquire the model data prior to the long-length imaging in order to obtain the approximate configuration. Then, a configuration data storage element 11a stores the configuration data of the signal intensity depending on the position along the move direction of the long-length imaging. Next, the long-length imaging is conducted by that the X-ray tube 2 irradiates X-ray to the subject M, the FPD 3 detects X-ray transmitted through the subject M, the FPD 3 respectively acquires and connects a plurality of X-ray images relative to the subject M while moving parallel to the data line 49 of the FPD 3, and the image connection element 9c generates the long-length image relative to the subject M. Relative to the X-ray image obtained by the long-length imaging as to the subject M, the overlapping pixel regions relative to two X-ray images (X-ray image number N, X-ray image number N+1) adjacent each other should naturally have the same brightness (pixel values) because the region thereof are adjacent images but the brightness difference (difference of pixel values) takes place due to the brightness variation (variation of pixel values) along the data line 49. Such difference is the variation of the offset value (offset correction value.) In this way, the difference Δ is acquired so that the variation depending on the position at the objective data line 49 can be acquired. In addition, the difference is acquired and the information relative to the subject M is canceled so that the brightness variation (pixel value variation) along the data line 49 can be purely acquired.

In addition, according to the configuration data of the signal intensity stored in the configuration data storage element 11a, the offset correction value calculation element 9a can calculate the offset correction value C relative to the pixels (i.e., pixel coordinate y) in the region other than such pixel regions, by substituting into the Formula (1), from the difference Δ of pixel values in such overlapping pixel regions described above. Further, the offset correction element 9b generates an X-ray image following each offset correction, which executes respectively the processing to subtract the offset value C on every data line 49 from the objective pixel values relative to the X-ray image (X-ray image number N), in place in the upper side of the move direction, of two adjacent X-ray images (X-ray image number N, X-ray image number N+1) each other relative to the subject M. The image connection element 9c connects the X-ray images, following the offset correction, acquired by such offset correction element 9b and generates the long-length imaging so that the long-length image, for which the X-ray images restricting the variation of brightness (pixel value variation) depending on the position of the gate line 49 are connected, can be obtained. As results, the long-length image naturally connected can be obtained.

The present invention is not limited to the aspect of Embodiment set forth above and furthers another alternative Embodiment can be implemented set forth below.

(1) The long-length imaging may be operable in the horizontal posture (recumbent posture), may be operable in the upright posture and may be operable in the tilted posture.

(2) According to the Embodiment described above, the present invention is not limited to the simple increase in linear configuration despite illustrating the Embodiment in which the signal intensity relative to the position along the move direction of the long-length imaging increased. The present invention can be applied according to the configuration data of the signal intensity depending on the position along the move direction of the long-length imaging, which is the model data obtained by using a phantom and so forth prior to the long-length imaging, can be depending on the position along the moving direction of the long-length imaging. Even if it is not a simple increase in the linear configuration, the model parameter (e.g., gradient) can be speculated by preparing a model configuration thereof in advance (e.g., quadric curve including parameters, and so forth) and conducting fitting and so forth based on the difference of pixel values in the overlapped pixel regions relative to two adjacent X-ray images each other relative to the subject. For example, when the signal intensity varies in the quadric curve relative to the position (along the move direction of the long-length imaging), since it is deemed that it varies in the quadric curve at the other location, the gradient a every data line can be speculated by preparing the model of the configuration data of the signal intensity with the offset correction value C as C=a×y2 (a is a gradient) and conducting fitting and so forth based on the difference described above every data line, respectively, so that each offset correction value C can be calculated.

REFERENCE OF SIGN

2 X-ray tube
3 Flat panel type X-ray detector (FPD)
9a Offset correction value calculation element
9b Offset correction element
9c Image connection element
11a Configuration data storage element
49 Data line
Δ Difference of pixel values in the overlapping pixel region
D Slot width
d Overlapping width
C Offset correction value
M Subject Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An X-ray imaging device, that conducts an X-ray imaging of a subject, comprises:
    an X-ray irradiation means that irradiates X-ray to a subject;
    a detection circuit that detects the X-ray transmitted through the subject;
    an X-ray detection means that acquires and connects a plurality of X-ray images while moving parallel to a defined data line of said X-ray detection means when said plurality of X-ray images acquired by said X-ray detection means are connected to generate a long-length image;
    a configuration data storage circuit that stores a configuration data of the signal intensity, which is a model data predetermined prior to the long-length imaging, depending on the position along a move direction of the long-length imaging;
    an offset correction value calculation circuit that calculates an offset correction value, depending on a position along the direction of the long-length imaging based on the configuration data of the signal intensity stored by the configuration data storage circuit and a difference of pixel values in an overlapping pixel region relative to two X-ray images adjacent each other with respect to the subject;
    an offset correction circuit that generates an X-ray image following each offset correction, and executes respectively the processing of every said data line, in which said offset correction value corresponding to a position of such a pixel is subtracted from the pixel value of said pixel relative to an X-ray image, in place in an upper side of a move direction, among two adjacent X-ray images with respect to said subject; and
    wherein an image connection circuit conducts said long-length imaging by connecting the X-ray images following the offset correction was provided by said offset correction circuit.

2. A method of operating an X-ray imaging device, comprising the steps of:
    providing an X-ray imaging device that conducts an X-ray imaging of a subject during a use;
    operating an X-ray irradiation means to irradiate an X-ray to a subject during said use;
    operating a detection means to detect the X-ray transmitted through the subject during said use;
    using an X-ray detection means to acquire and connect a plurality of X-ray images provided by said X-ray detection means while moving parallel to a defined data line of said X-ray detection means when said plurality of X-ray images are acquired by said X-ray detection means and are connected to thereby generate a long-length image during a long-length imaging;
    storing in a configuration data storage means that stores configuration data of a signal intensity, which is a model data predetermined prior to the long-length imaging, depending on a position defined along a move direction of the long-length imaging;
    calculating with an offset correction value calculation circuit to calculate an offset correction value depending on a position along the move direction of the long-length imaging based on the configuration data of the signal intensity stored by the configuration data storage means and a detected difference of pixel values in an overlapping pixel region relative to two X-ray images adjacent to each other with respect to the subject; and
    operating an offset correction circuit to generates an X-ray image following each offset correction, and executing respectively a processing of every data line in which said offset correction value corresponding to a position of such a pixel is subtracted from the pixel value of said pixel relative to an X-ray image, in place in an upper side of a move direction, among two adjacent X-ray images with respect to said subject; and
    operating an image connection circuit that conducts said long-length imaging by connecting the X-ray images following the offset correction provided by said offset correction circuit.

\* \* \* \* \*